(12) United States Patent
Watson

(10) Patent No.: US 6,482,446 B2
(45) Date of Patent: Nov. 19, 2002

(54) ASTRINGENT COMPOSITION AND METHOD OF USE

(75) Inventor: Geraldine A. Watson, Redondo Beach, CA (US)

(73) Assignee: Neutrogena Corporation, Los Angeles, CA (US)

(*) Notice: Subject to any disclaimer, the term of this patent is extended or adjusted under 35 U.S.C. 154(b) by 79 days.

(21) Appl. No.: 09/728,012

(22) Filed: Dec. 1, 2000

(65) Prior Publication Data

US 2002/0102314 A1 Aug. 1, 2002

(51) Int. Cl.$^7$ .................. A61K 35/78; A61K 7/021; A61K 7/06; A61K 31/80; A61K 31/27
(52) U.S. Cl. .................. 424/725; 424/63; 424/70.1; 424/78.03; 424/401; 424/405; 424/486; 424/488; 424/489; 424/744; 514/481; 514/492; 514/557
(58) Field of Search ............ 424/63, 70.1, 78.03, 424/401, 405, 486, 488, 489, 725, 744; 514/481, 492, 557

(56) References Cited

U.S. PATENT DOCUMENTS

| | | | |
|---|---|---|---|
| 4,569,839 A | * | 2/1986 | Grollier et al. |
| 4,840,798 A | | 6/1989 | Skaliotis |
| 4,973,473 A | | 11/1990 | Schneider et al. |
| 5,073,366 A | | 12/1991 | Beck |
| 5,871,764 A | | 2/1999 | Diaz et al. |

FOREIGN PATENT DOCUMENTS

| | | |
|---|---|---|
| EP | 0 273 202 B1 | 7/1988 |
| EP | 0 335 403 A2 | 10/1989 |
| WO | WO 93/21899 A1 | 11/1993 |
| WO | WO 97/14401 A1 | 4/1997 |
| WO | WO 98/50005 A1 | 11/1998 |
| WO | WO 00/47167 A1 | 8/2000 |

OTHER PUBLICATIONS

Peirce, A. Practical Guide to Natural Medicines, 1999. William Morrow and Co., Inc., New York, pp. 31–35.*
Japanese Abstract: XP–002192266 (JP 9124441) Derwent Publications Ltd.
Japanese Abstract: XP–002192267 (JP 4117314) Derwent Publications Ltd.
Wenninger and McEwen, International Ingredient Dictionary and Handbook, The Cosmetic, Toiletry, and Fragrance Assoc., Washington, D.C., 7$^{th}$ Ed., 1997, pp. 1565–1567, 1574–1575, 1628–1630, 1639–1640, 1650–1651, 1656–1670, 1693–1697.
EPO Search Report for European Patent Application No. 01310083.9 dated Mar. 27, 2002.

* cited by examiner

Primary Examiner—Christopher R. Tate
Assistant Examiner—Kailash C. Srivastava
(74) Attorney, Agent, or Firm—William E. McGowan

(57) ABSTRACT

The invention provides for astringent compositions comprising from about 0.1% to about 20% by weight of an astringent and between about 0.1% to 10% by weight of alcohol. The compositions have viscosity values of at least about 5,000 centipoise. The invention also provides for a method of using such compositions for delivering a topically active agent, such as salicylic acid, into skin.

23 Claims, No Drawings

ASTRINGENT COMPOSITION AND METHOD OF USE

FIELD OF THE INVENTION

The present invention relates to astringent compositions. The invention also relates to a method of using the compositions for delivering topically active agents into skin.

BACKGROUND OF THE INVENTION

Astringents are known in the art for use in tightening or binding soft tissue, and toning and moisturizing skin. Commercially available astringent compositions typically comprise very high amounts of alcohol, for example 35–45% by weight, and are liquids having a low viscosity. These compositions can be excessively drying and irritating to skin due to their high alcohol content. Additionally, the nature of their consistency and alcohol levels can make it difficult to control when applying. For example, if a consumer chooses to use only their hands for applying the astringent, then a greater volume and a larger application is needed for a targeted skin area due to the ease of astringent flow both during the transition from the container to one's hands and from one's hands to the targeted skin area. On the other hand, if a bath implement is used for applying the astringent, for example a cloth or cotton ball, then the thin consistency of the astringent results in some of the astringent being rapidly absorbed by the implement. Any absorbed astringent is then unavailable for use. Small quantities of astringent can also be lost through volatilization from its high alcohol levels.

The present invention provides for viscous and low alcohol content astringent compositions that can be used for delivering topically active agents into the skin.

SUMMARY FOR THE INVENTION

According to one aspect of the present invention there has now been provided an astringent composition including about 0.1% to about 20% by weight of an astringent and between about 0.1% to 10% by weight of an alcohol; wherein the composition has a viscosity of at least about 5,000 centipoise. In one embodiment, the composition further comprises a topically active agent, such as a keratolytic agent (e.g., salicylic acid) into skin. The present invention also features methods of using the above compositions.

Additional features and advantages of the present invention will be apparent from the detailed description of the invention and form the claims.

DETAILED DESCRIPTION OF THE INVENTION

It is believed that one skilled in the art can, based upon the description herein, utilize the present invention to its fullest extent. The following specific embodiments are to be construed as merely illustrative and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to astringent compositions having relatively low levels of alcohol and high viscosity values that, in one embodiment, can be used to deliver topically active agents into skin. In one embodiment, the composition comprises an astringent and an alcohol, wherein the composition has a viscosity of at least about 5,000 centipoise. While wishing not to be bound by a particular theory, it is believed that the high viscosity nature of the compositions provide occlusivity to skin, thereby holding the composition on the skin, while the alcohol delivers the topically active agent into the skin. The viscosity of the composition also assists in minimizing any loss of alcohol to the environment surrounding the application site, thereby enhancing the delivery of the active agent. As shown below in Example 3, it was also discovered that lower amounts of alcohol results in a greater percentage of active delivered from the composition into the skin as compared to compositions having higher amounts of alcohol.

Astringents are generally included in the compositions to help promote the binding and tightening of soft tissue and to tone skin. Any astringents known to one having ordinary skill in the art can be used in the present invention. Natural as well as synthetic astringents may be used. A representative, non-limiting list of natural astringents, include aluminum citrate, aluminum lactate, extracts of birch, extracts of coffee, extracts of evening primrose, extracts of grape, extracts of henna, extracts of ivy, extracts of lemon, and extracts of witch hazel. What is meant by an extract is either the whole fruit, bean, and/or plant or select constituents of such fruit, bean, and/or plant. The amount of astringent in the present invention is from about 0.1% to about 20% by weight, based on the total weight of the composition. In one embodiment, the astringent comprises an extract of witch hazel in an amount of about 10% by weight of the composition.

What is meant by the term "alcohol" is ethanol or isopropyl alchohol. Typically astringent compositions contain alcohol at levels of around 35–45% by weight. Compositions of the present invention comprise alcohol between about 0.1% to 10% by weight, preferably, less than about 5% by weight of the composition. Surprisingly, such low levels of alcohol were found to more effectively deliver active agents into the skin. As is shown in Example 3, astringent compositions containing about 5% ethanol delivered a greater percentage of an active agent into the skin than astringent compositions containing about 10% ethanol.

Compositions of the present invention have viscosity values of at least about 5,000 centipoise, preferably of at least about 10,000 centipoise. One embodiment of the present invention has a viscosity of about 12,500 centipoise. One means of obtaining the recited viscosity values is by adding a viscosity-increasing agent to the compositions, for example, a polyvinyl methacrylate/methyl acrylate crosspolymer. Other viscosity-increasing agents include, but are not limited to, bentonite, carbomer, carrageenan, ozokerite, dextrin, gelatin and cellulose resin such as xanthan gum. Additional viscosity-increasing agents are found in the International Cosmetic Ingredient Dictionary and Handbook, eds. Wenninger and McEwen, pp. 1693–1697 (The Cosmetic, Toiletry, and Fragrance Assoc., Washington, D.C., $7^{th}$ Ed., 1997) (hereinafter "ICI Handbook"). In one embodiment, the viscosity-increasing agent is present in an amount from about 0.02% to about 5% by weight of the composition.

Compositions of the present invention may further include topically active agents. What is meant by a "topically active agent" is a compound that has a cosmetic, prophylactic or therapeutic effect on the skin, e.g., agents to block UV rays, treat wrinkles and/or acne, or to lighten the skin. In one embodiment, the agent is selected from, but not limited to, the group consisting of hydroxy acids, benzoyl peroxide, sulfur resorcinol, ascorbic acid, D-panthenol, hydroquinone, sunscreen agents, keratolytic agents, anti-inflammatory agents, skin lightening agents, antimicrobial and antifungal agents, estrogens, 2-dimethylaminoethanol, lipoic acid, amino acids such a proline and tyrosine, lactobionic acid, acetyl-coenzyme A, niacin, riboflavin, thiamin, ribose, electron transporters such as NADH and FADH2, botanical extracts such as aloe vera and soy, and derivatives and mixtures thereof. The topically active agent will typically be present in the composition of the invention in an amount between about 0.01% to about 20% by weight of the composition.

Examples of hydroxy acids include, but are not limited, to (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

In a preferred embodiment, the topically active agent is a keratolytic agent. Exemplary karatolytic agents are salicylic acid, boric acid and methyl salicylate. Compositions of the present invention comprise a keratolytic agent in an amount from about 0.1% to about 5% by weight, preferably from about 0.5% to about 2% by weight of the composition. In one embodiment salicylic acid is present in an amount of about 2% by weight of the composition.

Solubilizers for the optional topically active agent may also be employed. Preferably, such solubilizers are oil-free, compatible with alcohol, and do not crystallize the topically active agent. Examples of solubilizers include, but are not limited to, polyethylene glycol, polyethylene glycol ethers of fatty alcohols, and mixtures thereof. Solubilizers are present in amounts sufficient to solubilize such topically active agent(s).

In one embodiment, the compositions further comprises a skin-soothing agent Exemplary skin-soothing agents are extracts from Aloe Vera and Chamomile and mixtures thereof. Skin-soothing agents are typically present in amounts from about 0.1% to about 5% by weight of the composition In preferred embodiments, the composition comprises less than 1%, by weight, of oil or does not comprise any oil. What is meant by the term "oil" is an animal (e.g., fatty acid esters), mineral (e.g., parafinic oils), vegetable (e.g., vegetable oils), or synthethic hydrocarbons that are liquid at room temperature, soluble in organic solvents, and substantially not soluble in water (e.g., less than 0.1 mg/ml at 25°). Examples of oils include but are not limited to: mineral oils such as paraffinic oils; synthetic hydrocarbons such as polybutene and polyisobutene; vegetable oils such as castor oils, sesame oils, and peanut oils; and animal oils and fats such as triglycerides and butters. Other examples of fats, oils, and hydrocarbons are found in the International Cosmetic Ingredient Dictionary and Handbook, eds. Wenninger and McEwen, pp.1565–67 and 1574–75 of the ICI Handbook.

The novel compositions of the present invention may also contain other cosmetic ingredients such as humectants, emollients, skin-conditioning agents, skin protectants, colorants, fragrances and the like. Examples of such may be found on pages 1628–1630, 1639–1640, 1650–1651, 1656–1670 of the ICI Handbook.

The compositions of the present invention may be applied to the skin (e.g., the face of a human). In one embodiment, the composition may be applied once or twice a day. In one embodiment, the composition is applied to the skin by first applying to the hands and then rubbing it onto the target skin area. In another embodiment, the composition is applied to a bath implement, such as a cotton ball or a cloth, and then applied to the target skin area.

The following is a description of the manufacture and testing of astringent compositions. Other compositions of the present invention can be prepared in an analogous manner by a person of ordinary skill in the art.

EXAMPLE 1

A substantially oil-free astringent composition (formulation A) was made with the following ingredients and corresponding amounts.

| Ingredient | Weight Percentage |
| --- | --- |
| Purified water | q.s. 100 |
| Polyvinyl methacrylate/methyl acrylate crosspolymer | 1.8 |
| Allantoin | 0.08 |
| Chloeth-24 & Ceteth-24 (50:50) | 0.2 |
| Salicylic acid | 2 |
| Glycereth-7 | 2 |
| Polyethylene glycol-4 | 1 |
| Dimethicone copolyol | 1 |
| Hexylene glycol | 2 |
| Witch hazel | 10 |
| Benzophenone-4 | 0.03 |
| Sodium hydroxide (50%) | 1.5 |
| Sodium PCA | 1 |
| Menthol | 0.05 |
| Extract of Aloe Vera | 0.2 |
| Extract of Chamomile | 0.2 |
| Ethanol mixture (95% ethanol) | 5 |
| Colorant | q.s. |
| Fragrance | q.s. |

Formulation A was made by the following procedure. Approximately 80–90% of the quantity of purified water was heated to 75° C., and the allantoin and polyvinyl methacrylate/methyl acrylate crosspolymer were added thereafter. These ingredients were mixed for approximately 30 minutes. Chloeth-24 and Cetheh-24 were then added, and the batch mixed until all of the solids were dissolved. Following this, the batch was cooled to about 50–55° C. Next, the salicylic acid, glycereth-7, PEG-4, and dimethicone copolyol were added, with continuous mixing sufficient to completely dissolve the salicylic acid. Hexylene glycol was then added, thereby dropping the batch temperature, whereupon witch hazel (Manamelis Viginiana (containing 14% ethanol); The EE Dickinson Company, Essex, Connecticut, USA) was added when the temperature reached about 40–45° C. Benzophenone-4, sodium hydroxide, and the remaining portion of purified water were added with 3 minutes of mixing between each addition. The batch was mixed until a homogenous blend was achieved. With the batch at 40° C., sodium PCA, menthol, and the natural extracts of Aloe Vera and Chamomile were added, with 3 minutes of mixing between each addition. The batch was then allowed to cool to 35° C., whereupon the ethanol mixture (SD-40 Alcohol; Quantum Chemical, Cincinnati, Ohio, USA) was added. Lastly, the colorant and fragrance were added with 5 minutes of mixing between each addition.

EXAMPLE 2

A second astringent composition (formulation B) was made with the difference from example 1 above being the addition of about 10% by weight of the ethanol mixture as compared to about 5% by weight of the ethanol mixture.

EXAMPLE 3

Penetration studies were conducted on eight panelists to determine the amount of salicylic acid that had penetrated into their skin. The amount of salicylic acid was determined using a Perking Elmer Specrofluorometer (Norwalk, Conn., USA) equipped with a fiber optic probe. Specific areas on the subjects' skin were monitored at time zero, 3 hours, and 6 hours after the initial application, and subsequently wiping off the product from the applied areas. Suprisingly, a greater percentage of salicylic acid penetrated the skin with the product having the lower amount of alcohol as shown in the table below.

| Product | % Penetration v. Form. A, after 3 hours | % Penetration v. Form. A, after 6 hours |
| --- | --- | --- |
| Formulation A (5% alcohol) | 100 | 100 |
| Formulation B (10% alcohol) | 86 | 93 |

EXAMPLE 4

Compositions of the present invention have viscosity values of at least about 5,000 centipoise. Viscosity measurements taken from formulation A are shown in the table below. A Brookfield RVT Spindle TB viscometer (Stoughton, Mass., USA) was used for evaluating the viscosity of the samples. The samples were surrounded by a water bath environment at a temperature of 25° C. A Helipath drive motor was used to rotate a T-bar spindle just above the surface of each sample. The Helipath drive was started in the downward direction, with a reading taken every rotation. After 6 readings were recorded, the direction of the Helipath drive was reversed, and 6 additional readings were taken, one per rotation of the spindle. The values shown in the table below are averages from the 12 readings. The compositions are somewhat thixotropic in nature, resulting in viscosity creep over time.

| Age, time after batch completion | Viscosity, cps |
| --- | --- |
| 1 hour | 11,960 |
| 18 hours | 11,993 |
| 24 hours | 12,120 |
| 2 days | 12,120 |
| 3 days | 12,133 |
| 4 days | 12,446 |
| 7 days | 12,580 |

It is understood that while the invention has been described in conjunction with the detailed description thereof, that the foregoing description is intended to illustrate and not limit the scope of the invention, which defined by the scope of the appended claims. Other aspects, advantages, and modifications are within the claims.

What is claimed is:
1. An astringent composition comprising:
 (a) from about 0.1% to about 20% by weight of an astringent wherein the astringent is not an alcohol;
 (b) between about 0.1% to 10% by weight of an alcohol; and
 (c) salicylic acid;
 wherein said composition has a viscosity of at least about 5,000 centipoise.
2. The composition of claim 1, wherein said astringent is selected from the group consisting of an extract of witch hazel, aluminum citrate, aluminum lactate, extract of birch, extract of coffee, extract of evening primrose, extract of grape, extract of henna, extract of ivy, extract of lemon, and mixtures thereof.
3. The composition of claim 1, wherein said astringent is an extract of witch hazel.
4. The composition of claim 1, wherein said composition comprises from about 0.02% to about 5% by weight of a viscosity-increasing agent.
5. The composition of claim 4, wherein said viscosity increasing agent is polyvinyl methacrylate/methyl acrylate crosspolymer.
6. The composition of claim 1 having a viscosity of at least about 10,000 centipoise.
7. The composition of claim 1, wherein said alcohol is ethanol.
8. The composition of claim 1, wherein the said alcohol is ethanol and said alcohol is less than about 5% by weight of the composition.
9. The composition of claim 6, wherein the said alcohol is ethanol and said alcohol is less than about 5% by weight of the composition.
10. The composition of claim 1, wherein the amount of said salicylic acid is from about 0.5% to about 2% by weight of the composition.
11. The composition of claim 1 further comprising a solubilizer in an amount servable to solubilize said salicylic acid.
12. The composition of claim 11, wherein said solubilizer is selected from the group consisting of polyethylene glycol, polyethylene glycol ethers of fatty alcohols, and mixtures thereof.
13. The composition of claim 1 further comprising from about 0.1% to about 5% by weight of a skin soothing agent, wherein said skin soothing agent is selected from the group consisting of extracts of Aloe Vera, extracts of Chamomile, and mixtures thereof.
14. The composition of claim 1, wherein said composition comprises less than 1%, by weight, of oil.
15. The composition of claim 6, wherein said astringent is an extract of witch hazel.
16. The composition of claim 7, wherein said astringent is an extract of witch hazel.
17. The composition of claim 8, wherein said astringent is an extract of witch hazel.
18. The composition of claim 9, wherein said astringent is an extract of witch hazel.
19. The composition of claim 9, wherein the amount of salicylic acid is from about 0.5% to about 2% by weight of the composition.
20. The composition of claim 11, wherein said astringent is an extract of witch hazel.
21. The composition of claim 10, wherein said astringent is an extract of witch hazel.
22. The composition of claim 5, wherein said agent is an extract of witch hazel.
23. The composition of claim 19, wherein said astringent is an extract of witch hazel.

* * * * *

UNITED STATES PATENT AND TRADEMARK OFFICE
CERTIFICATE OF CORRECTION

PATENT NO. : 6,482,446 B2
DATED : November 19, 2002
INVENTOR(S) : Geraldine A. Watson It is certified that error appears in the above-identified patent and that said Letters Patent is hereby corrected as shown below:

<u>Column 6,</u>
Line 34, please delete the word "servable" and insert therefore the word -- suitable --
Line 64, please delete the word "agent" and insert therefore the word -- astringent --

Signed and Sealed this

Seventh Day of September, 2004

JON W. DUDAS
*Director of the United States Patent and Trademark Office*